United States Patent
Mesana et al.

(10) Patent No.: US 12,350,148 B2
(45) Date of Patent: *Jul. 8, 2025

(54) STENTED HEART VALVE DEVICES AND METHODS FOR ATRIOVENTRICULAR VALVE REPLACEMENT

(71) Applicant: Medtronic, Inc., Minneapolis, MN (US)

(72) Inventors: Thierry Mesana, Ottawa (CA); Timothy G. Laske, Shoreview, MN (US); Alexander Hill, Blaine, MN (US); Timothy Ryan, Minnetrista, MN (US); Allen Tower, North Lawrence, NY (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/063,239

(22) Filed: Dec. 8, 2022

(65) Prior Publication Data

US 2023/0107234 A1   Apr. 6, 2023

Related U.S. Application Data

(60) Continuation of application No. 16/922,666, filed on Jul. 7, 2020, now Pat. No. 11,534,295, which is a
(Continued)

(51) Int. Cl.
*A61F 2/06* (2013.01)
*A61F 2/24* (2006.01)
(Continued)

(52) U.S. Cl.
CPC .......... *A61F 2/2418* (2013.01); *A61F 2/2433* (2013.01); *A61F 2/82* (2013.01);
(Continued)

(58) Field of Classification Search
CPC ........ A61F 2/2418; A61F 2/2436; A61F 2/82; A61F 2002/825; A61F 2002/826;
(Continued)

(56) References Cited

U.S. PATENT DOCUMENTS 3,939,402 A   2/1976   Mogilevsky et al.
4,340,977 A   7/1982   Brownlee et al.
(Continued)

FOREIGN PATENT DOCUMENTS

EP   0554082 A1   8/1993
EP   0916362 A1   5/1999
(Continued)

OTHER PUBLICATIONS http://dictionary.reference.com/browse/edge?s=t printed on Jun. 11, 2015, 1 page.
(Continued)

*Primary Examiner* — Ann Hu

(57) ABSTRACT

A compressible and expandable stent assembly for implantation in a body lumen such as a mitral valve, the stent assembly including at least one stent barrel that is shaped and sized so that it allows for normal operation of adjacent heart structures. One or more stent barrels can be included in the stent assembly, where one or more of the stent barrels can include a cylinder with a tapered edge.

19 Claims, 6 Drawing Sheets

Related U.S. Application Data division of application No. 15/338,124, filed on Oct. 28, 2016, now Pat. No. 10,736,737, which is a division of application No. 12/009,323, filed on Jan. 17, 2008, now Pat. No. 9,510,943.

(60) Provisional application No. 60/881,351, filed on Jan. 19, 2007.

(51) Int. Cl.
   *A61F 2/82*      (2013.01)
   *A61F 2/848*     (2013.01)
   *A61F 2/852*     (2013.01)
   *A61F 2/958*     (2013.01)

(52) U.S. Cl.
   CPC ........ *A61F 2/958* (2013.01); *A61F 2002/065* (2013.01); *A61F 2002/8486* (2013.01); *A61F 2/852* (2013.01); *A61F 2210/0014* (2013.01); *A61F 2220/0008* (2013.01); *A61F 2220/0016* (2013.01); *A61F 2230/0008* (2013.01); *A61F 2230/001* (2013.01); *A61F 2230/0017* (2013.01); *A61F 2230/005* (2013.01); *A61F 2230/0054* (2013.01); *A61F 2250/0018* (2013.01); *A61F 2250/0036* (2013.01); *A61F 2250/0037* (2013.01); *A61F 2250/0039* (2013.01); *A61F 2250/0064* (2013.01); *A61F 2250/0069* (2013.01)

(58) Field of Classification Search
   CPC .......... A61F 2/852; A61F 2/958; A61F 2/962; A61F 2210/0014; A61F 2220/0008; A61F 2220/0016; A61F 2230/0054; A61F 2250/0037; A61F 2250/0039
   See application file for complete search history.

(56) References Cited

U.S. PATENT DOCUMENTS

| | | |
|---|---|---|
| 4,655,771 A | 4/1987 | Wallsten |
| 5,409,495 A | 4/1995 | Osborn |
| 5,411,552 A | 5/1995 | Andersen et al. |
| 5,554,184 A | 9/1996 | Machiraju |
| 5,554,185 A * | 9/1996 | Block ............... A61F 2/2412 623/2.12 |
| 5,800,520 A * | 9/1998 | Fogarty ............... A61F 2/915 623/1.37 |
| 5,893,887 A * | 4/1999 | Jayaraman ............. A61F 2/915 623/1.15 |
| 5,906,641 A | 5/1999 | Thompson et al. |
| 5,938,697 A | 8/1999 | Killion et al. |
| 6,086,612 A | 7/2000 | Jansen |
| 6,090,140 A * | 7/2000 | Gabbay ............... A61F 2/2412 623/2.11 |
| 6,110,201 A | 8/2000 | Quijano et al. |
| 6,136,023 A | 10/2000 | Boyle |
| 6,287,336 B1 | 9/2001 | Globerman et al. |
| 6,346,089 B1 * | 2/2002 | Dibie ............... A61F 2/954 623/1.11 |
| 6,425,916 B1 | 7/2002 | Garrison et al. |
| 6,485,524 B2 | 11/2002 | Strecker |
| 6,491,719 B1 | 12/2002 | Fogarty et al. |
| 6,508,833 B2 | 1/2003 | Pavcnik et al. |
| 6,641,609 B2 | 11/2003 | Globerman |
| 6,656,219 B1 | 12/2003 | Wiktor |
| 6,709,440 B2 | 3/2004 | Callol et al. |
| 6,673,109 B2 | 6/2004 | Cox |
| 6,773,455 B2 | 8/2004 | Allen et al. |
| 6,932,837 B2 * | 8/2005 | Amplatz ............... A61F 2/90 623/1.53 |
| 7,159,592 B1 | 1/2007 | Makower et al. |
| 7,169,176 B2 * | 1/2007 | Lauterjung ............. A61F 2/07 623/2.38 |
| 7,276,078 B2 * | 10/2007 | Spenser ............... A61F 2/2418 623/1.24 |
| 7,588,596 B2 | 9/2009 | Spiridigliozzi et al. |
| 7,674,284 B2 * | 3/2010 | Melsheimer ........... A61F 2/07 623/1.13 |
| 8,430,902 B2 * | 4/2013 | Bergheim ............. A61F 2/2476 128/898 |
| 9,402,754 B2 * | 8/2016 | Chan ................. A61F 2/915 |
| 2001/0021872 A1 | 9/2001 | Bailey et al. |
| 2002/0032481 A1 * | 3/2002 | Gabbay ............... A61F 2/2418 623/2.14 |
| 2002/0183830 A1 | 12/2002 | Su et al. |
| 2003/0024527 A1 | 2/2003 | Ginn |
| 2003/0036791 A1 | 2/2003 | Philipp et al. |
| 2003/0114913 A1 | 6/2003 | Spenser et al. |
| 2003/0195614 A1 | 10/2003 | Ryan et al. |
| 2003/0199963 A1 | 10/2003 | Tower et al. |
| 2003/0199971 A1 | 10/2003 | Tower et al. |
| 2004/0044400 A1 | 3/2004 | Cheng et al. |
| 2004/0049262 A1 | 3/2004 | Obermiller et al. |
| 2004/0206363 A1 | 10/2004 | Mccarthy et al. |
| 2004/0210306 A1 | 10/2004 | Quijano et al. |
| 2005/0075731 A1 * | 4/2005 | Artof ............... A61F 2/2439 623/2.18 |
| 2005/0203610 A1 | 9/2005 | Tzeng |
| 2005/0209687 A1 | 9/2005 | Sitzmann et al. |
| 2005/0240258 A1 | 10/2005 | Bolduc et al. |
| 2005/0256566 A1 | 11/2005 | Gabbay |
| 2006/0025857 A1 | 2/2006 | Bergheim et al. |
| 2006/0047297 A1 | 3/2006 | Case |
| 2006/0259137 A1 | 11/2006 | Artof et al. |
| 2007/0005127 A1 | 1/2007 | Boekstegers et al. |
| 2007/0055356 A1 * | 3/2007 | Eidenschink ............. A61F 2/07 623/1.25 |
| 2007/0150042 A1 * | 6/2007 | Balaji ............... A61F 2/82 623/1.13 |
| 2007/0173932 A1 | 7/2007 | Cali et al. |
| 2008/0097595 A1 * | 4/2008 | Gabbay .............. A61B 17/3417 604/532 |
| 2008/0183273 A1 | 7/2008 | Mesana et al. |
| 2009/0248143 A1 | 10/2009 | Laham |
| 2009/0319022 A1 | 12/2009 | Hartley et al. |
| 2010/0298927 A1 * | 11/2010 | Greenberg ............. A61F 2/2418 623/1.25 |
| 2013/0166023 A1 * | 6/2013 | Pipenhagen .......... A61F 2/2418 623/2.17 |
| 2020/0078162 A1 | 3/2020 | Chobotov et al. |

FOREIGN PATENT DOCUMENTS

| | | | | |
|---|---|---|---|---|
| EP | 1057460 A1 | 12/2000 | | |
| EP | 1075824 A1 | 2/2001 | | |
| FR | 2870716 A1 | 12/2005 | | |
| WO | WO-9313825 A1 * | 7/1993 | ............... | A61F 2/88 |
| WO | 0172240 A1 | 10/2001 | | |
| WO | 2005023153 A2 | 3/2005 | | |
| WO | 2005046526 A1 | 5/2005 | | |
| WO | WO-2006085304 A2 * | 8/2006 | ............... | A61F 2/95 |

OTHER PUBLICATIONS http://dictionary.reference.com/browse/taper?s=t printed on Jun. 11, 2015, 1 page.
http://dictionary.reference.com/browse/cylinder?s=t printed on Jun. 11, 2015, 1 page.
Extended European Search Report dated Aug. 9, 2013, 11 pages.
Philipp Bonhoeffer et al., "Percutaneous Insertion of the Pulmonary Valve," Journal of the American College of Cardiology 2002; 39: 1664-1669.
Philipp Bonhoeffer et al., "Transcatheter Implantation of a Bovine Valve in Pulmonary Position," Circulation 2000; 102: 813-816, Mar. 16, 2000.

\* cited by examiner

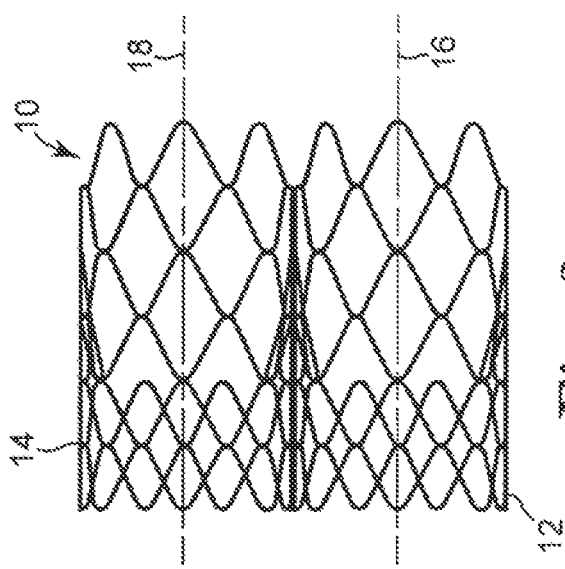
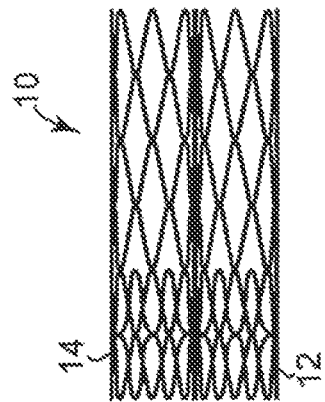
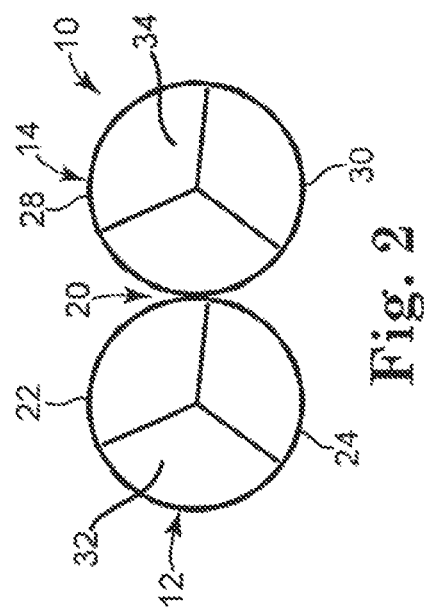
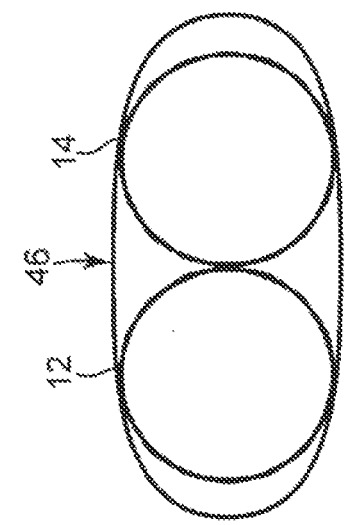
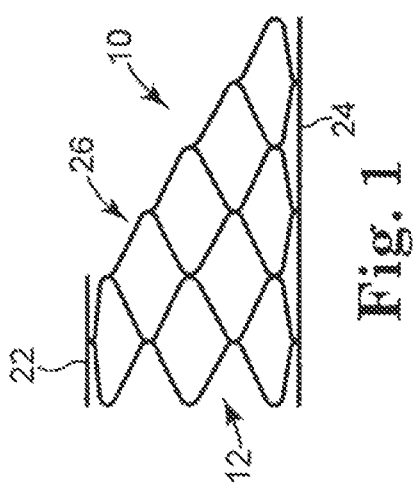
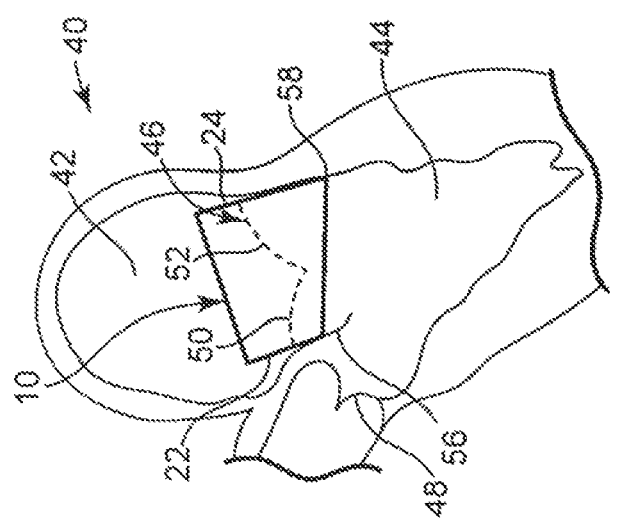

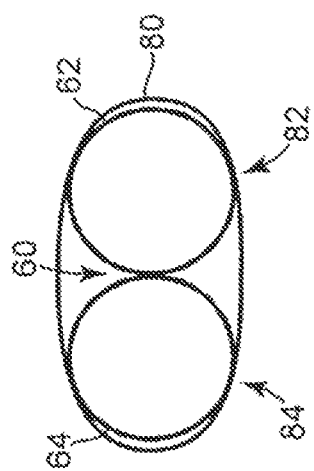
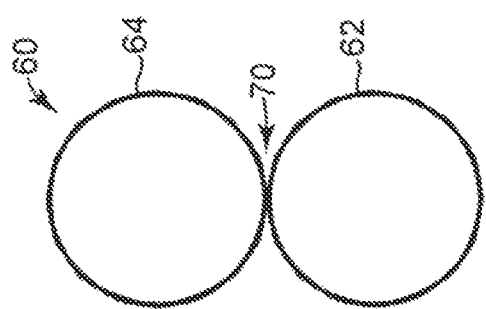
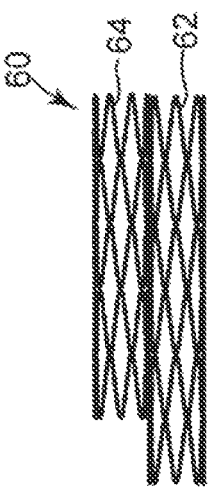
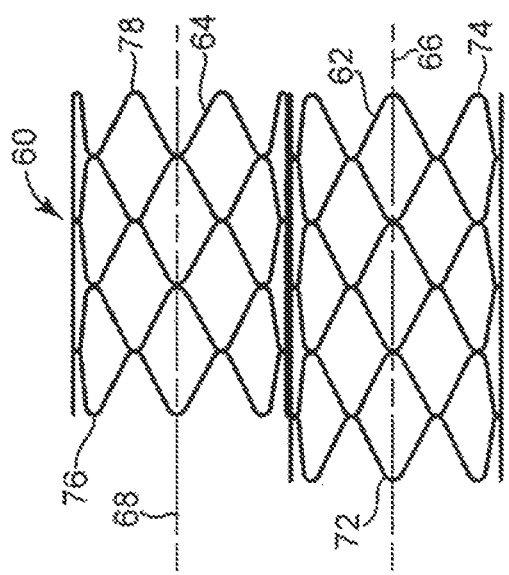
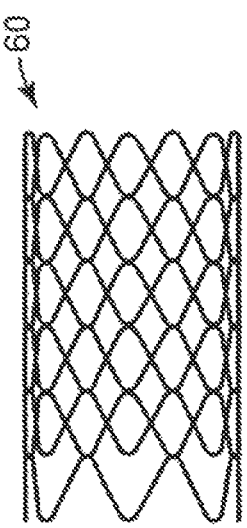

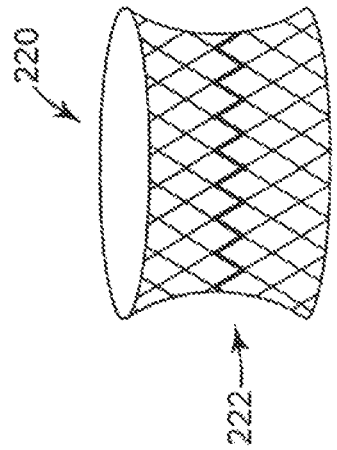
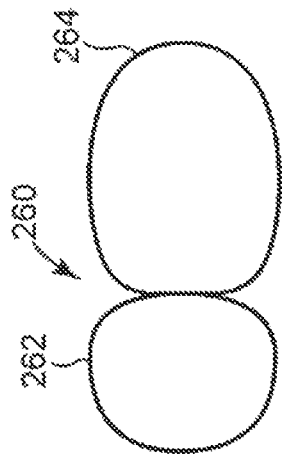
Fig. 24
Fig. 27
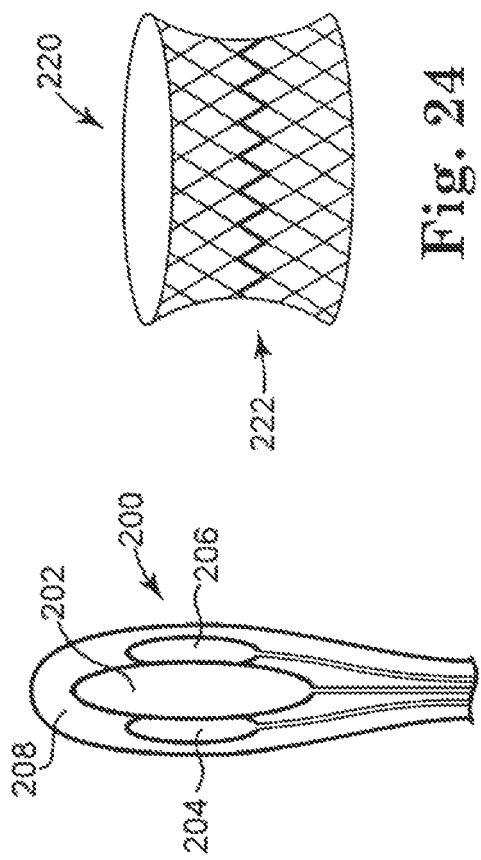
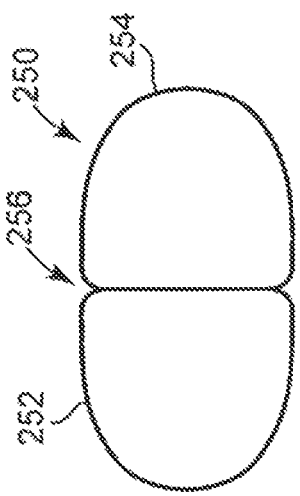
Fig. 23
Fig. 26
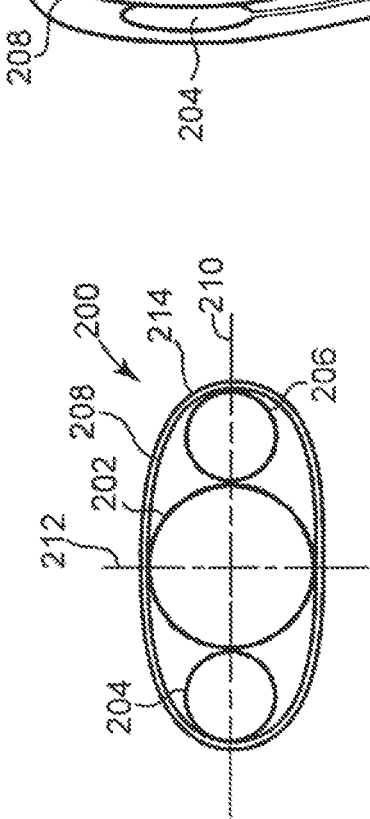
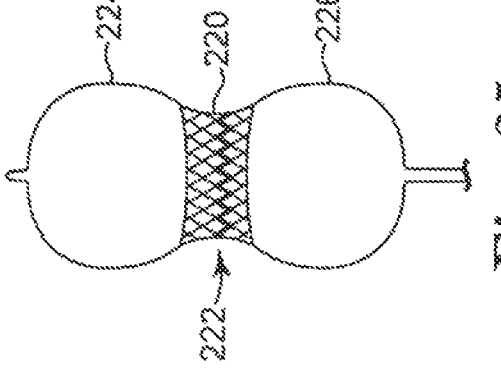
Fig. 22
Fig. 25

STENTED HEART VALVE DEVICES AND METHODS FOR ATRIOVENTRICULAR VALVE REPLACEMENT

CROSS-REFERENCE TO RELATED APPLICATION

The present application is a continuation of and claims priority to U.S. patent application Ser. No. 16/922,666, filed Jul. 20, 2020, now U.S. Pat. No. 11,534,295, which is a Division of and claims priority to U.S. patent application Ser. No. 15/338,124, filed Oct. 28, 2018, now U.S. Pat. No. 10,736,737, which is a Division of and claims priority to U.S. patent application Ser. No. 12/009,323, filed Jan. 17, 2008, now U.S. Pat. No. 9,510,943, which claims priority to U.S. Provisional Application No. 60/881,351, filed Jan. 19, 2007, the entire contents of each of which are incorporated herein by reference in their entirety.

TECHNICAL FIELD

The present invention relates generally to devices and methods for repair of heart valves, and more particularly to prosthetic heart valves for use in replacement of the mitral valve.

BACKGROUND

One of the two atrio-ventricular valves in the heart is the mitral valve, which is located on the left side of the heart and which forms or defines a valve annulus and valve leaflets. The mitral valve is located between the left atrium and the left ventricle, and serves to direct oxygenated blood from the lungs through the left side of the heart and into the aorta for distribution to the body. As with other valves of the heart, the mitral valve is a passive structure in that it does not itself expend any energy and does not perform any active contractile function.

The mitral valve includes two moveable leaflets that open and close in response to differential pressures on either side of the valve. Ideally, the leaflets move apart from each other when the valve is in an open position, and meet or "coapt" when the valve is in a closed position. However, problems can develop with valves, which can generally be classified as either stenosis, in which a valve does not open properly, or insufficiency (also called regurgitation), in which a valve does not close properly. Stenosis and insufficiency may occur concomitantly in the same valve. The effects of valvular dysfunction vary, with mitral regurgitation or backflow typically having relatively severe physiological consequences to the patient. Regurgitation, along with other abnormalities of the mitral valve, can increase the workload placed on the heart. The severity of this increased stress on the heart and the patient, and the heart's ability to adapt to it, determine the treatment options that are available for a particular patient. In some cases, medication can be sufficient to treat the patient, which is the preferred option when it is viable; however, in many cases, defective valves have to be repaired or completely replaced in order for the patient to live a normal life.

One situation where repair of a mitral valve is often viable is when the defects present in the valve are associated with dilation of the valve annulus, which not only prevents competence of the valve but also results in distortion of the normal shape of the valve orifice. Remodeling of the annulus is central to these types of reconstructive procedures on the mitral valve. When a mitral valve is repaired, the result is generally a reduction in the size of the posterior segment of the mitral valve annulus. As a part of the mitral valve repair, the involved segment of the annulus is diminished (i.e., constricted) so that the leaflets may coapt correctly on closing, and/or the annulus is stabilized to prevent post-operative dilatation from occurring. Either result is frequently achieved by the implantation of a prosthetic ring or band in the supra annular position. The purpose of the ring or band is to restrict, remodel and/or support the annulus to correct and/or prevent valvular insufficiency. Such repairs of the valve, when technically possible, can produce relatively good long-term results.

However, valve repair is sometimes either impossible or undesirable or has failed, such as in cases where dilation of the valve annulus is not the problem, leaving valve replacement as the preferred option for improving operation of the mitral valve. In cases where the mitral valve is replaced, the two general categories of valves that are available for implantation are mechanical valves and bioprosthetic or tissue valves. Mechanical valves have been used for many years and encompass a wide variety of designs that accommodate the blood flow requirements of the particular location where they will be implanted. Although the materials and design features of these valves are continuously being improved, they do increase the risk of clotting in the blood stream, which can lead to a heart attack or stroke. Thus, mechanical valve recipients must take anti-coagulant drugs for life to prevent the potential of blood clots. Further, mechanical valves can sometimes suffer from structural problems that may force the patient to have additional surgeries for further valve replacement. On the other hand, the use of tissue valves provides the advantage of not requiring anti-coagulant drugs, although tissue valves do not typically last as long as mechanical valves. Thus, tissue valves may wear out and need to be replaced after a number of years. The surgical procedure for implantation of many of these mechanical and tissue valves typically involves opening the patient's chest to access the mitral valve through the left atrium, and sewing the new valve in position.

To simplify surgical procedures and reduce patient trauma, there has been a recent increased interest in minimally invasive and percutaneous replacement of cardiac valves. Replacement of a heart valve typically does not involve actual physical removal of the diseased or injured native heart valve. Rather, the replacement valve is delivered in a compressed condition to the native valve site, where it is expanded. One example of such a valve replacement system includes inserting a replacement pulmonary valve into a balloon catheter and delivering it percutaneously via the vascular system to the location of a failed pulmonary valve. There, the replacement valve is expanded by a balloon to compress the native valve leaflets against the right ventricular outflow tract, thereby anchoring and sealing the replacement valve. In the context of percutaneous pulmonary valve replacement, U.S. Patent Application Publication Nos. 2003/0199971 A1 and 2003/0199963 A1, both filed by Tower, et al., describe a valved segment of bovine jugular vein, mounted within an expandable stent, for use as a replacement pulmonary valve. As described in the articles: "Percutaneous Insertion of the Pulmonary Valve", Bonhoeffer, et al., Journal of the American College of Cardiology 2002; 39: 1664-1669 and "Transcatheter Replacement of a Bovine Valve in Pulmonary Position", Bonhoeffer, et al., Circulation 2000; 102: 813-816, the replacement pulmonary valve may be implanted to replace native pulmonary valves or prosthetic pulmonary valves located in valved conduits. Other implantables and implant delivery devices also are disclosed in published U.S. Patent Application Publication No. 2003/0036791 A1 and European Patent Application No. 1 057 460-A1.

There is a continued desire to be able to be able to improve mitral valve replacement devices and procedures to accommodate the physical structure of the heart without causing undue stress to the patient during the operation on the heart, such as providing devices and methods for replacing the mitral valve percutaneously.

SUMMARY

One embodiment of the invention includes a compressible and expandable stent assembly for implantation in a body lumen. The stent assembly comprises a first stent barrel comprising a tubular structure that is compressible and expandable in a radial direction and that comprises an outer surface having a periphery, wherein a first portion of the periphery of the first stent barrel has a first length and a second portion of the periphery of the first stent barrel has a second length that is less than the first length, and further wherein the first stent barrel comprises a tapered edge that extends from the first portion of the periphery of the first stent barrel to the second portion of the periphery of the first stent barrel. Thus, the first stent barrel essentially includes a sloped surface between the first and second portions of the stent barrel when the stent is viewed from the side. The stent assembly further includes a second stent barrel adjacent to and extending from the first stent barrel, wherein the second stent barrel comprises a tubular structure that is compressible and expandable in a radial direction and that comprises an outer surface having a periphery, wherein a first portion of the periphery of the second stent barrel has a first length and a second portion of the periphery of the second stent barrel has a second length that is less than the first length, and further wherein the second stent barrel comprises a tapered edge that extends from the first portion of the periphery of the second stent barrel to the second portion of the periphery of the second stent barrel. Again, the second stent barrel essentially includes a sloped surface between the first and second portions of the stent barrel when the stent is viewed from the side.

Another embodiment of the invention includes a compressible and expandable stent assembly for implantation in a body lumen, wherein the stent assembly comprises a first stent barrel comprising a first length and a tubular structure that is compressible and expandable in a radial direction and a second stent barrel comprising a second length that is less than the first length and a tubular structure that is compressible and expandable in a radial direction, wherein the second stent barrel is adjacent to and extends from the first stent barrel along a tangential line that extends in a generally perpendicular direction to the radial expansion direction of the first and second stent barrels.

The invention further includes a method of positioning a stent assembly into the mitral valve area of a patient, the method comprising the steps of providing a stent assembly comprising a first stent barrel having an outer peripheral surface and a first length, and a second stent barrel having an outer peripheral surface that is adjacent to and extending from the outer peripheral surface of the first stent barrel, wherein the second stent barrel has a second length that is greater than the first length, and positioning the stent assembly in the mitral valve area so that the first stent barrel is adjacent to an anterolateral portion of the mitral valve and the second stent barrel is adjacent to a posteromedial portion of the mitral valve, wherein the length of the first stent barrel minimizes interference with the functioning of an adjacent aortic valve and provides enough contact area to impede dislodging of the stent assembly.

The invention further includes a delivery system for delivering a stent to a body lumen and expanding the stent, the delivery system comprising a first axis, a second axis perpendicular to the first axis, an expandable central balloon comprising first and second opposite sides and centered on the intersection of the first and second axes, a first expandable side balloon positioned adjacent to the first side of the central balloon and centered on the first axis, and a second expandable side balloon positioned adjacent to the second side of the central balloon and centered on the first axis, wherein a first width of the device measured along the first axis is greater than a second width of the device measured along the second axis.

In addition, the invention includes a compressible and expandable tubular stent comprising a first end, an opposite second end, and a central portion between the first and second ends, wherein the central portion comprises a reinforced area extending around at least a portion of a periphery of the stent.

BRIEF DESCRIPTION OF THE DRAWINGS

The present invention will be further explained with reference to the appended Figures, wherein like structure is referred to by like numerals throughout the several views, and wherein:

FIG. 1 is a side view of one embodiment of a stent in accordance with the invention, with the stent in its at least partially expanded condition;

FIG. 2 is a top plan view of the stent of FIG. 1 with exemplary valve leaflets in their closed positions;

FIG. 3 is a front plan view of the stent of FIG. 1;

FIG. 4 is a schematic sectional view of a portion of the heart, with the stent of FIGS. 1-3 positioned within the annulus of the mitral valve;

FIG. 5 is a top schematic view of a mitral valve annulus with the stent of FIG. 2 positioned therein;

FIG. 6 is a front plan view of the stent of FIG. 3, with the stent shown in a compressed condition;

FIG. 7 is a front view of another embodiment of a stent in accordance with the invention, with the stent shown in its at least partially expanded condition;

FIG. 8 is a top plan view of the stent of FIG. 7;

FIG. 9 is a side view of the stent of FIG. 7;

FIG. 10 is a front view of the stent of FIG. 7, with the stent shown in a compressed condition;

FIG. 11 is a top schematic view of a mitral valve annulus with the stem of FIG. 8 positioned therein;

FIG. 22 is a top plan view of another exemplary delivery system positioned within a stent of the invention;

FIG. 23 is a cross-sectional side view of a delivery system of the type shown in FIG. 22;

FIG. 24 is a perspective view of another alternative embodiment of a stent in accordance with the invention;

FIG. 25 is a schematic side view of the stent of FIG. 24 being expanded by a delivery system for positioning within a patient;

FIG. 26 is a top plan view of an exemplary two-barreled stent assembly having non-circular stent shapes; and FIG. 27 is a top plan view of an exemplary two-barreled stent assembly having stents that have different sizes.

DETAILED DESCRIPTION

Figure 13:
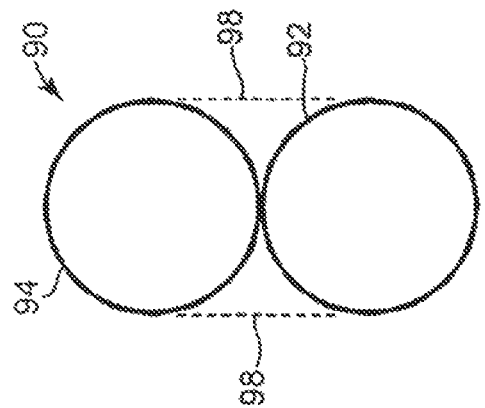
FIG. 13 is a top plan view of the stent of FIG. 12.

Referring now to the Figures, wherein the components are labeled with like numerals throughout the several Figures, and initially to FIGS. 1-3, one embodiment of a mitral stent assembly 10 in accordance with the invention is illustrated. Although the stents of the invention, such as stent assembly 10, are described herein as being used for mitral valve replacement, it is understood that many of the features of these stents can be used for valves in other areas of the heart. For example, the stents of the invention may be used for replacement of the tricuspid valve, where the configuration of such a stent may be identical or slightly different than described herein for replacement of the mitral valve due to the different anatomy in that area of the heart. In any case, the stents of the invention desirably restore normal functioning of a cardiac valve, and can be implanted percutaneously or using surgical techniques that include minimally invasive methods or more traditional open-heart surgical methods.

Stent assembly 10 includes a first stent barrel 12 and a second stent barrel 14, which are arranged so that a longitudinal axis 16 of stent barrel 12 is generally parallel to a longitudinal axis 18 of stent barrel 14, although the longitudinal axes 16, 18 may be at least slightly angled relative to each other. Stent barrel 12 is attached to stent barrel 14 along at least a portion of its length at an intersection or common area 20. In this embodiment, stent barrel 12 is tapered along its length, such that the stent barrel 12 is shorter at a first edge 22 than at a second edge 24. As can be seen in FIGS. 1 and 2, first edge 22 is essentially the uppermost edge along the length of the stent barrel 12, and second edge 24 is the lowermost edge along the length of the stent barrel 12 and on the opposite side of the barrel 12 from the first edge 22. Stent barrel 12 further includes a tapered edge 26 that extends from the first edge 22 to the second edge 24, which can be a relatively straight or smooth slope when viewed from the side, as shown, or instead may be an edge that is curved or otherwise shaped between the edges 22, 24. For example, tapered edge 26 may essentially be either concave or convex in shape. Due to the spacing of the wires from each other and the configuration of such wires, the tapered edge 26 may be staggered, such as in a stair-step type of arrangement, rather than being smooth.

Because the stent barrel 12 is relatively cylindrical in shape, the edge 26 can be considered to be curvilinear between the edges 22,24 when viewed in perspective. The length of second edge 24 may be only slightly longer than the length of first edge 22, or may be considerably longer, depending on the patient anatomy and other factors, as will be described in further detail below. The difference between the lengths of these two edges 22, 24 will be a determining factor in the slope of the edge 26 extending between them.

Stent barrel 14 of the stent assembly 10 is identical or nearly identical in size and shape to the stent barrel 12, and thus includes a first edge 28 that is essentially the uppermost edge along the length of the stent barrel 14, which corresponds to the first edge 22 of stent barrel 12. Stent barrel 14 further includes a second edge 30 that is essentially the lowermost edge along the length of the stent barrel 14 and on the opposite side of the barrel 14 from the first edge 28, which corresponds to the second edge 24 of stent barrel 12. Stent barrel 14 further includes a tapered edge (not visible in the illustrated views) that extends from the first edge 28 to the second edge 30 opposite its first edge and generally corresponds to tapered edge 26 of stent barrel 12. The tapered edge of stent barrel 14 is not visible in these Figures (e.g., FIG. 1), because it has approximately the same positioning (e.g., length, angle, etc.) as the tapered edge 26 of stent barrel 12 and thus is obscured by the same features of stent barrel 12 in FIG. 1. However, it is contemplated that this edge, along with other features of the stent barrel 14, can be slightly or substantially different from corresponding features of the stent barrel 12 within a single stent assembly 10. This "double-barrel" arrangement of connected stents provides a stent arrangement that can at least roughly match the size and shape of the interior opening of the native valve in which it is positioned.

The stent barrels of the invention, such as stent barrels 12, 14, as shown and described relative to the figures, can correspond generally to a stent of the type described in the above-cited Tower, et al. and Bonhoeffer et al. references, for example, although it is understood that a wide variety of stent configurations can be used in accordance with the invention. The stent barrels may be fabricated of platinum, stainless steel, Nitinol, an alloy of the type commercially available under the trade designation MP35N, or other biocompatible metal. The stent barrels of the invention may alternatively be fabricated using wire stock as described in the above-cited Tower, et al. applications, or the stent barrels may be produced by machining or laser cutting the stent from a metal tube, as is commonly employed in the manufacturing of stents. The number of wires, the positioning of such wires, and various other features of the stem can vary considerably from that shown in the figures. The specifics of the stent barrels can vary widely within the scope of the invention, such that many other known generally cylindrical or cuff-like stent configurations may be used and are considered to be within the scope of the invention.

In any case, the stent barrels of the invention are preferably compressible to a relatively small diameter for insertion into a patient, but are also at least slightly expandable from this compressed condition to a larger diameter when positioned in a desired location in the patient. It is further preferable that the process of compressing the stent barrels does not permanently deform the stent barrels in such a way that expansion thereof would be difficult or impossible. That is, each stent barrel should be capable of maintaining a desired structural integrity after being compressed and expanded. With the embodiments of the invention that include two barrels connected or attached to each other, these manufacturing techniques may be modified to fabricate both stents as an integral unit, if desired.

The stent barrels of the invention, like most expandable and compressible cylindrical stents, generally take the form of a series of zigzag or sinusoidal ring structures. These structures are coupled longitudinally to one another to form a generally cylindrical-shaped structure, although it is understood that the structures can be arranged in an at least slightly oval or elliptical shape. Each ring structure takes the form of a series of adjacent generally straight sections that meet one another at one end at a curved or angled junction to form a "V" or "U" shaped structure. It should also be understood that stent barrels used according to the present invention may employ ring structures coupled to one another at all or fewer than all of the bases of their "V"s, or coupled to one another by additional and/or different structures, such as longitudinal members of the type disclosed in U.S. Pat. No. 6,773,455, issued to Allen, et al., U.S. Pat. No. 6,641,609, issued to Globerman, and U.S. Pat. No. 6,136,023, issued to Boyle. The invention also includes within its scope stent barrels in which wires are formed into zigzags and wound spirally to produce a cylindrical structure, as in U.S. Pat. No. 6,656,219, issued to Wiktor, or woven stents as disclosed in U.S. Pat. No. 4,655,771, issued to Wallsten.

Stent barrels of the type described above can be assembled into a mitral or tricuspid stented valve assembly in accordance with the methods of the invention described herein. One exemplary method for assembling a stented valve generally first includes preparation of a vein segment, then a subsequent mounting or attachment of the prepared vein segment to the stent, using a variety of mounting or attachment techniques. FIG. 2 illustrates the stent assembly 10 with a three-leaflet valve 32, 34 positioned within each of the stent barrels 12, 14, respectively. This three-leaflet arrangement is exemplary; alternative configurations include a bi-leaflet valve positioned in both of the stent barrels, and valves that are different from each other in each of the stent barrels (e.g., one of the stent barrels includes a three-leaflet valve while the other barrel includes a bi-leaflet valve). In any case, the multi-barreled stent configurations of the invention advantageously allow for replacement of only one of the valves if there is a valve failure at some point after implantation, while the properly functioning valve remains operational.

The stent assemblies of the invention may use a preserved bovine jugular vein of the type described in the above-cited Bonhoeffer, et al. and Tower, et al. references. However, other vessels or donor species may alternatively be used, and in order to provide additional valve strength in the relatively high-pressure conditions that exist in the mitral valve area of the heart, pericardial valves, polymeric valves, or metallic valves may alternatively be used in a tricuspid or bicuspid leaflet configuration.

FIG. 6 illustrates the stent assembly 10 with stent barrels 12, 14 in an at least partially compressed condition. The stent barrels 12, 14 may be compressed in this manner prior to implantation in a patient, for example, and can be expanded into the mitral or tricuspid valve space during the surgical procedure.

As described above, stent barrels 12, 14 are connected to or extend from each other at common area 20. The stent barrels may be connected along their entire lengths at the common area 20, or may instead be attached along only a portion of their lengths. In one exemplary embodiment, the stent barrels 12, 14 may be manufactured as separate components, then bonded, adhered, welded, or otherwise attached to each other at one or more points along the length of common area 20. In order to provide additional flexibility between the stent barrels 12, 14, they may be attached or intertwined with each other a limited number of the rows of stent wires. Alternatively, to provide less flexibility between the stent barrels 12, 14, they may be attached or intertwined at every point where they contact or are otherwise adjacent to each other along their lengths. In another example, the stent barrels 12, 14 may be manufactured or assembled in such a way that the wires of the stent barrels 12, 14 are woven to intersect or connect in this area during the formation of those two barrels. In this embodiment, the barrels 12, 14 are formed as portions of an integrated wire structure and therefore are not formed as separate components that need to be attached or secured to each other. In yet another example, two separate stent barrels are positioned in a desired location relative to each other, then a separate device or structure, such as a mechanical strut, is positioned for attachment to both stent barrels, thereby connecting them to each other in a double-barrel system of the type shown.

As shown in the figures and as is briefly described above, first edge 22 of stent barrel 12 is shorter than second edge 24 of stent barrel 12. The lengths of these two portions are designed to be different in order to accommodate certain anatomical structures, which are described with further reference to FIGS. 4 and 5.

FIG. 4 illustrates a portion of a heart 40, with a stent assembly 10 of the invention positioned therein. In particular, heart 40 includes a left atrium 42, a left ventricle 44, a mitral valve 46 and an aortic valve 48. The broken lines of mitral valve 46 illustrate its native leaflets as they would generally be configured in a closed position prior to implantation of stent assembly 10. In particular, mitral valve 46 includes a first leaflet 50 on the anterior side of the valve, and a second leaflet 52 on the posterior side of the valve. When mitral valve 46 is operating properly, the native leaflets 50, 52 will generally function in such a way that blood flows toward the left ventricle 44 when the leaflets 50, 52 are in an open position, and so that blood is prevented from moving toward the left atrium 42 when the leaflets 50, 52 are in a closed position. However, stent assembly 10 can be positioned in the area of mitral valve 46 when it is not functioning properly (to replace the mitral valve) in accordance with the invention, thereby pushing the leaflets 50, 52 out of the mitral valve space, such as are shown as leaflets 56 and 58, respectively. In this view, first stent barrel 12 is visible; however, the second stent barrel 14 would be positioned immediately behind stent barrel 12.

In this embodiment, first edge 22 of stent barrel 12 is positioned to move leaflet 50 on the anterior side of the valve out of the mitral valve space and to its position shown as leaflet 56, and second edge 24 of stent barrel 12 is positioned to move leaflet 52 on the posterior side of the valve out of the mitral valve space and to its position shown as leaflet 58. In order to not block the flow of blood through the aortic valve 48, the first edge 22 of stent barrel 12 is provided with a length that is sufficiently short so that it does not push the leaflet 56 to a position in which it will interfere with blood flow through the aortic valve 48 and/or interfere with the actual movement or functioning of the leaflets of the aortic valve 48. However, first edge 22 of stent barrel 12 further is provided with a sufficient length to provide a suitable area of contact with the annulus of the mitral valve to help to maintain it in its desired position. Thus, as shown, one embodiment of the stent barrel 12 includes a top portion that extends into the left atrium 42 and a lower portion that moves the leaflet 36 out of the mitral valve space, yet allows a portion of leaflet 36 to extend freely beyond the first edge 22. The amount of the leaflet 56 that extends beyond the bottom of stent barrel 12 is preferably small enough that it does not substantially and/or detrimentally interfere with the functioning of the aortic valve 48. It is noted that the structure, features, and positioning of the stent barrel 14 of the stent assembly 10 can be similar or identical to that of stent barrel 12.

FIGS. 7-11 illustrate another exemplary embodiment of a stent assembly 60 of the invention, which includes a first stent barrel 62 and a second stent barrel 64, which are arranged so that a longitudinal axis 66 of stent barrel 62 is generally parallel to a longitudinal axis 68 of stent barrel 64. Stent barrel 62 is connected to stent barrel 64 along at least a portion of its length at a common area 70. In this embodiment, stent barrel 62 is not tapered along its length, but instead extends as a continuous cylinder shape from its first end 72 to its second end 74. Similarly, stent barrel 64 is not tapered along its length, but instead extends as a continuous cylinder shape from a first end 76 to a second end 78. As shown in the figure, the distance between first and second ends 72, 74 is greater then the distance between first and second ends 76, 78 so that the first stent barrel 62 is longer than the second stent barrel 64. The diameters of the first and second stent barrels 62, 64 can be essentially the same as each other when expanded, or may be different, depending on the anatomy of the patient in which the stent assembly will be implanted, the implantation techniques used, and other factors.

As is shown best in FIG. 7, the second end 74 of first stent barrel 62 is generally aligned with the second end 78 of second stent barrel 64, while first end 72 of first stent barrel 62 is offset relative to the first end 76 of second stent barrel 64; however, it is contemplated that the second ends 74, 78 of these stent barrels are not aligned, but instead are also offset from each other. In other words, stent barrel 64 can be positioned in a different relative location along the length of stent barrel 62 in such a way that none of the ends of the stent barrels 62, 64 are aligned with each other.

FIG. 11 illustrates stent assembly 60 positioned within the annulus of an exemplary mitral valve 80. In this configuration, the shorter stent barrel 64 is adjacent to an anterolateral portion 84 of mitral valve 80 and the longer stent barrel 62 is adjacent to a posteromedial portion 82 of mitral valve 80. In this way, interference of the stent assembly 60 with the functioning of the aortic valve and left ventricular outflow tract will be minimized, in accordance with the invention. Thus, the stent barrel 64, which is adjacent to the anterolateral portion 84 of the mitral valve 80, preferably is sufficiently short to minimize interference with the functioning of the aortic valve, yet is sufficiently long to provide enough contact area between the barrel 64 and the annulus to lessen the chances that the stent assembly 60 will become dislodged once it has been implanted. The stent barrel 62, which is adjacent to the posteromedial portion 82 of the mitral valve 80, can have any appropriate length that provides sufficient contact area with the annulus to lessen the chance that the stent assembly 60 will become dislodged once it has been implanted.

Similarly, if the stents of the invention are positioned within the annulus of a triscuspid valve, the shorter barrel (e.g., stent barrel 64 of FIG. 7) or the shorter side of a tapered barrel (e.g., first edge 22 of stent barrel 12 of FIG. 1) is preferably aligned with or adjacent to the anterior annulus of the tricuspid valve and/or the septal annulus of the tricuspid valve and/or the anteroseptal commissure of the tricuspid valve.

FIG. 10 illustrates stent assembly 60 with the first and second stent barrels 62, 64 in their compressed conditions. In order to insert the stent assembly 60 into the patient's heart, the stent assembly may desirably be compressed to such a condition in order to aid in less invasive surgical techniques. When the stent assembly 60 is compressed, stent barrels 62, 64 may lengthen at least slightly as compared to their uncompressed or expanded states, or may remain essentially the same length, depending on the construction of the stent barrels 62, 64. Exemplary devices and methods for delivering the stent assembly in such a compressed condition will be explained in further detail below.

It is also contemplated that one or both of the first and second stent barrels 62, 64 can include a tapered edge, a flared edge, or the like, such as is discussed above relative to edge 26 of FIGS. 1,5. For one example, a stent assembly may include two stent barrels having different lengths, where the shorter barrel is additionally provided with a tapered edge to further minimize interference with the leaflet that is closest to the aortic valve. Alternatively, both of the stent barrels could have tapered edges, even if they have different lengths.

Figure 12:
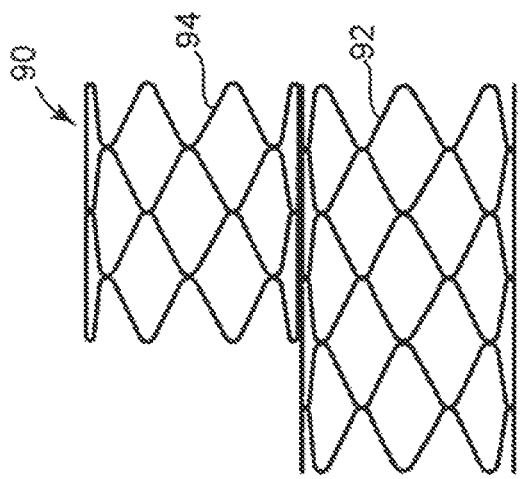
FIG. 12 is a front view of another embodiment of a stent in accordance with the invention, with the stent in its at least partially expanded condition.
Figure 14:
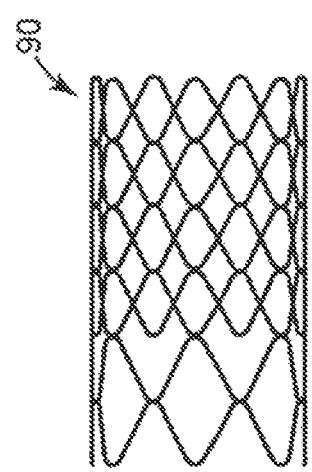
FIG. 14 is a side view of the stent of FIG. 12.

FIGS. 12-14 illustrate another exemplary embodiment of a stent assembly 90 of the invention, which includes a first stent barrel 92 and a second stent barrel 94 that are connected or extend from each other along at least a portion of their lengths. As with the embodiment of FIG. 7, the first stent barrel 92 is longer than the second stent barrel 94; however, in this embodiment the second stent barrel 94 is proportionally even shorter relative to the first stent barrel 92 as compared to the length relationship between the stent barrels 62, 64 of stent assembly 60. That is, the difference between the lengths of the barrels is greater than in the embodiment of FIG. 7. Otherwise, this embodiment of stent assembly 90 is substantially the same as that of the stent assembly 60, and the same variations and options described above are also contemplated for this embodiment. The differences in the lengths of the two stent barrels within a particular stent assembly of the invention may be greater or smaller than that shown in the Figures.

The stent assemblies described herein that include more than one stent barrel are generally shown and described as including stent barrels that are cylindrical, oval, or elliptical in shape; however, a number of different stent shapes are also contemplated. One exemplary alternative configuration is illustrated in FIG. 26 with stent assembly 250, which includes a first stent barrel 252 and a second stent barrel 254. Each of these two stent barrels has a curvilinear surface (which can be designed to generally match the shape of the ends of the annulus of a mitral valve) and a generally flat or planar surface that results in more "squared off" corners where the flat surface meets the curvilinear surface. The flat surfaces of the stent barrels 252, 254 are attached or extend from each other at a central area 256. This arrangement provides more potential connection points between the two stent barrels since the surface area of contact is larger than is provided when two cylindrical stents are brought in contact with each other.

Another exemplary configuration is illustrated in FIG. 27 with stent assembly 260, which includes a first stent barrel 262 and a second stent barrel 264, where the second stent barrel 264 is larger than the first stent barrel 262. In addition, each of these stent barrels is shown to include a portion that is somewhat flat and in contact with a flat portion of the other stent barrel, although it is also contemplated that these stent barrels have curvilinear surfaces that are in contact with each other, basically along a tangent line. With this embodiment and others described herein, it is possible to insert each of the two or more stent barrels separately into the patient, and then attach them to each other while they are inside the patient. The attachment between the stent barrels can be accomplished through the use of cooperating mechanical attachment (e.g., barbs, hooks, or the like), magnetic attraction, adhesives, or other methods that allow for permanent or semi-permanent attachment of the stent barrels to each other. With continued reference to FIG. 27, it is also contemplated that a first stent barrel (e.g., stent barrel 264) can be inserted into the patient and expanded to a first outer perimeter that is relatively large, and then a second stent barrel (e.g., stent barrel 262) is inserted adjacent to the first stent barrel and expanded so that the expansion of the second stent barrel causes at least a slight compression of the first stent barrel. The two stent barrels can be attached to each other either before, during, or after expansion of the second stent barrel FIGS. 15-18 illustrate yet another embodiment of a stent assembly of the invention. In particular, a stent assembly 100 is shown, which includes a single stent barrel 102. The single barrel device can be used in a native valve, in a valve previously repaired with an annuloplasty band or ring, or in a valve replaced with a bioprosthetic device. Stent barrel 102 is tapered along its length, similar to the stent barrels described above relative to FIGS. 1-5. In particular, stent barrel 102 is shorter at a first edge 104 than at a second edge 106, wherein first edge 104 is shown as the uppermost edge along the length of stent barrel 102, and second edge 106 is shown as the lowermost edge along the opposite side of the barrel 102 from the first edge 104. Stent barrel 102 further includes a tapered edge 108 that extends from the first edge 104 to the second edge 106. Edge 108 can be relatively straight or smooth when viewed from the side, as shown, or instead may be an edge that is curved or otherwise shaped between the edges 104, 106. Due to the spacing of the wires from each other and the configuration of such wires, the tapered edge 108 may be staggered, such as in a stair-step type of arrangement, rather than being smooth. Because the barrel 102 is relatively cylindrical in shape, the edge 108 is actually curvilinear between the edges 104, 106 when viewed in perspective. The length of second edge 106 may be only slightly greater than the length of first edge 104, or may be considerably longer, or even be equal in length, as desired and/or depending on the patient anatomy. This stent assembly 100 includes only a single stent barrel as compared to the dual-barrel embodiments described above; however, the tapered edge provides certain similar advantages to those of the dual-barrel design.

Figure 18:
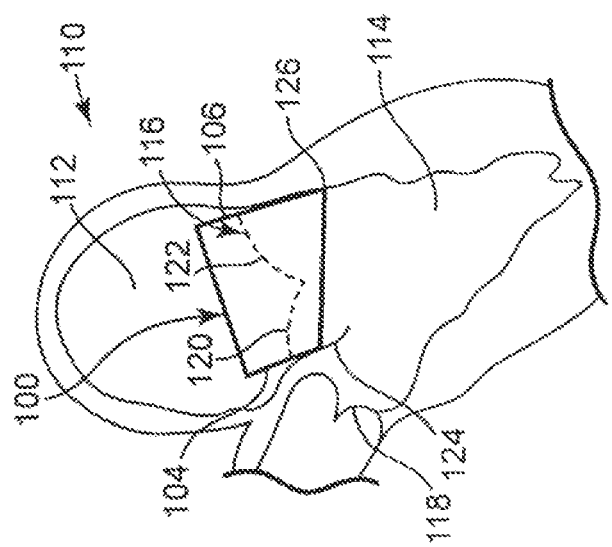
FIG. 18 is a schematic sectional view of a portion of the heart, with the stent of FIG. 15 positioned within the annulus of the mitral valve.
Figure 15:
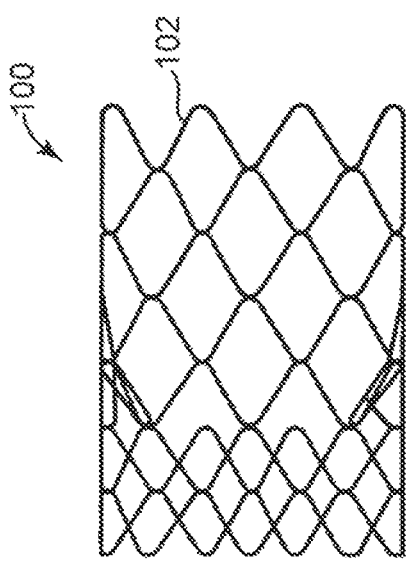
FIG. 15 is a front view of another embodiment of a stent in accordance with the invention.
Figure 17:
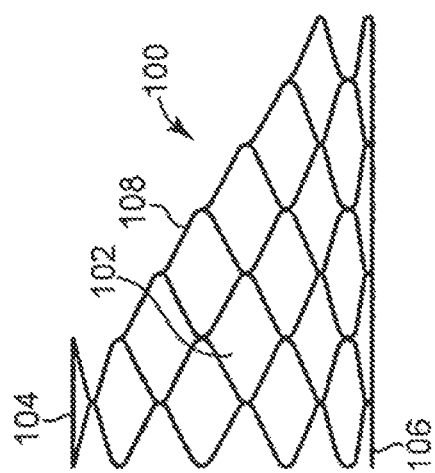
FIG. 17 is a side view of the stent of FIG. 15.

As with the stent assembly 10 described above, the lengths of these two edges 104, 106 of stent assembly 100 are designed to be different in order to accommodate certain anatomical structures, which are described with further reference to FIG. 18. This figure illustrates a portion of a heart 110, with a stent assembly 100 of the invention positioned therein. In particular, heart 110 includes a left atrium 112, a left ventricle 114, a mitral valve 116, and an aortic valve 118. The broken lines of mitral valve 116 illustrate its leaflets as they would generally be configured prior to implantation of stent assembly 100. In particular, mitral valve 116 includes a first leaflet 120 on the anterior side of the valve, and a second leaflet 122 on the posterior side of the valve.

Stent assembly 100 can be positioned at the area of mitral valve 116 when it is not functioning properly (to replace the mitral valve), thereby pushing the first and second native leaflets 120, 122 out of the mitral valve space, such as are shown as leaflet 124 and 126, respectively. As shown, first edge 104 is positioned to move leaflet 120 on the anterior side of the valve out of the mitral valve space and to its position shown as leaflet 124, and second edge 106 of stent barrel 102 is positioned to move leaflet 122 on the posterior side of the valve out of the mitral valve space and to its position shown as leaflet 126. In order to not block the flow of blood through the aortic valve 118, the first edge 104 of stent barrel 102 is provided with a length that is sufficiently short so that it does not push the leaflet 124 to a position in which it will interfere with blood flow through the aortic valve 118 and/or interfere with the actual movement or functioning of the leaflets of the aortic valve 118; however, first edge 104 is further provided with a sufficient length to provide a suitable area of contact with the annulus of the mitral valve to help to maintain it in its desired position. Thus, as shown, one embodiment of the stent barrel 102 includes a top portion that extends into the left atrium 112 and a lower portion that moves the leaflet 124 out of the mitral valve space, yet allows a portion of leaflet 124 to extend freely beyond its lower edge. The amount of the leaflet 124 that extends beyond the bottom of stent barrel 102 is preferably small enough that it does not substantially and/or detrimentally interfere with the functioning of the aortic valve 118.

Stent barrel 102, along with any of the other stent barrels of the present invention, may be configured so that they are relatively circular in cross section when in their expanded condition, as shown in the Figures. However, it is also possible that the stent barrels of the invention are at least slightly elliptical, oval, D-shaped, square, or differently shaped in cross-section when in their expanded condition. In the case of the single barrel design of the stent assembly 100, such a non-circular shape may be provided for the stent barrel in order to accommodate the shape of the mitral valve annulus, for example. That is, the shape of the stent assemblies can be designed and selected to provide both positional stability and a proper fit to the patient's anatomy.

Figure 16:
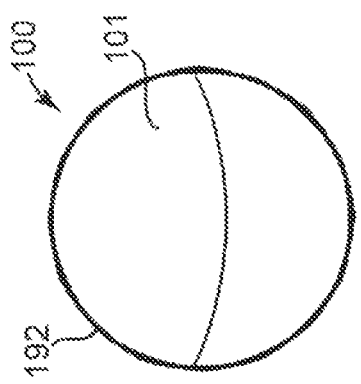
FIG. 16 is a top plan view of the stent of FIG. 15 with valve leaflets in their closed positions.

To make the stent barrel 102 into a stented valve that can be used to replace the mitral valve, one or more valve segments are attached within the stent barrel 102 using techniques known in the art for attaching valve segments within a stent. For example, FIG. 16 illustrates stent assembly 100 with a two-leaflet valve 101 positioned within stent barrel 102. In the case of such a two-leaflet valve, the leaflets may be attached in a generally central location in order to prevent prolapse of the leaflets into the atrium. However, another leaflet configuration may alternatively be used, such as a three-leaflet valve.

If more than one valve segment is to be attached within a single stent barrel, the multiple valve segments may further be attached to each other where they are adjacent to each other in the stent assembly. Alternatively, the stent barrel may be provided with a center strut or support portion that spans across the open portion of the stent barrel, thereby dividing the center portion into two generally "D" shaped areas into which valve segments can be attached, for example. These areas can be the same or a different size and shape from each other, depending on where the center strut or support portion is positioned.

Figure 20:
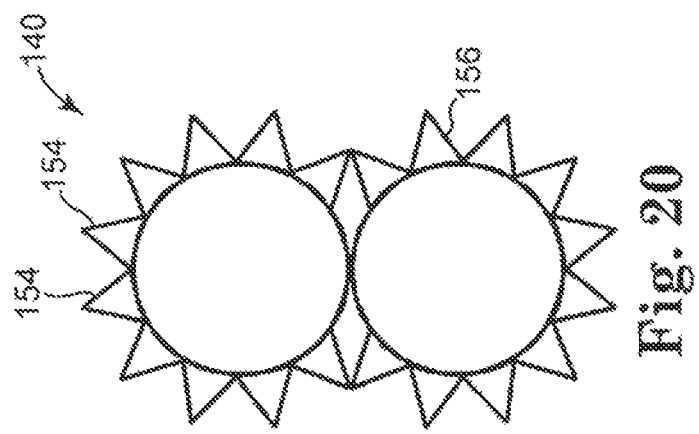
FIG. 20 is a top plan view of the stent of FIG. 19.
Figure 19:
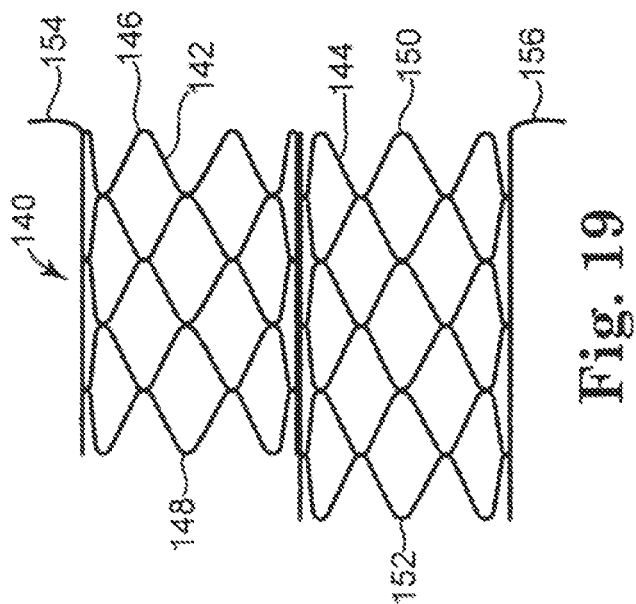
FIG. 19 is a front view of another embodiment of a stent in accordance with the invention, including multiple flange portions.

FIGS. 19 and 20 illustrate a docking or positioning feature that can optionally be used with any of the stent barrels of the invention, and is shown with particular use on a stent assembly 140. Stent assembly 140 includes a first stent barrel 142 and a second stent barrel 144 that is longer than the first stent barrel 142. First stent barrel 142 includes a first end 146 and a second end 148, and second stent barrel 144 includes a first end 150, which is generally aligned with the first end 146 of stent barrel 142, and a second end 152, which is offset from the second end 148 of first stent barrel 142. First stent barrel 142 further includes at least one flange portion 154 extending from the stent structure at the first end 146. In the exemplary embodiment shown, one flange portion 154 extends from all or most of the points of each "V" structure at the first end 146, although it is contemplated that the stent barrel 142 include any number of flange portions 154. These flange portions 154 may be made of the same wire-type material from which the stent barrel 142 is made, and the flanges may be integrally molded or formed with the stent assembly 140. Alternatively, the flange portions 154 may be made of a different material and/or may comprise separate structures that are attached or connected to the structure of stent barrel 142. The flange portions 154 may also have a different size or shape than the triangular or V-shaped structures illustrated. For example, the flange portions 154 may be semi-circular, rectangular, oblong, or the like, and may be considerably smaller or larger than shown. In yet another variation, a different flange structure can be provided that is more continuous around the periphery of the stent barrel 142 (i.e., does not comprise a series of adjacent flanges).

In addition to or as an alternative to the flange portions 154 provided on the stent barrel 142, the second stent barrel 144 may include at least one flange portion 156 extending from the stent structure at its first end 150. The features and configurations described above relative to flange portions 154 are also contemplated for use with the flange portion(s) 156. These flange portions 156 may be the same as or different than the flange portions 154 in structure, shape, size, and the like, depending on the particular configuration and use of the stent assembly 140.

In any case, the flange portion(s) 154 and/or 156 are preferably configured to be shaped and sized to provide an anchoring function for the stent assembly 140 when it is positioned to replace a valve. Referring to FIG. 4, for example, if stent assembly 140 were positioned within the mitral valve annulus in a similar manner to how stent assembly 10 is positioned within heart 40, any flange portions that extend from the stent assembly 140 can provide interference with the walls of the left atrium 42, thereby inhibiting motion of the stent assembly 140.

Any of the stent assemblies discussed herein can further include structures that provide a fixation function for securing the stent assembly in its desired location. For example, the stent assembly can include hooks, barbs, or the like that attach to a valve annulus upon deployment of the stent assembly.

The stent assemblies of the invention may further include a cover or other material to prevent blood leakage into undesired areas of the heart. For example, the stent assemblies that include two stent barrels may include a cover (e.g., tissue, polymer, or biocompatible fabric) that spans the area between the barrels on one or both sides of the stent assembly and/or covers the entire outer periphery of the stent barrels. Such a cover 98 is illustrated in broken lines in FIG. 13, and is shown on both sides of the stent assembly 90.

Figure 21:
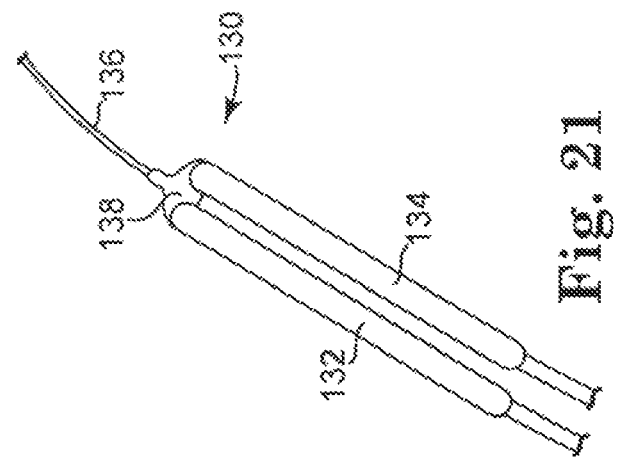
FIG. 21 is a side view of a portion of an exemplary delivery system that can be used in the surgical implantation of the stents of the invention.

Any of the stent assemblies described above can be used for percutaneous insertion and implantation of a replacement heart valve in replacement of a defective or malfunctioning valve. A portion of an exemplary system 130 that can be used to implant a double-barrel stent of the types described above is illustrated in FIG. 21. System 130 includes an elongated balloon catheter having two inflatable balloons 132, 134 that are separated from each other near the distal end of the system 130. Balloons 132, 134 are connected for fluid communication with separate lumens that extend through the length of the catheter. These lumens provide for independent inflation and deflation of the balloons 132, 134 with a fluid, such as a radio-opaque fluid, during the process of deploying a stent assembly within a patient. System 130 further includes a thin guide wire 136 that extends generally along the length of the catheter. The guide wire 136 may be, for example, a 0.089 cm diameter extra stiff guidewire as manufactured by Amplatzer of Golden Valley, Minnesota, which may be used in a conventional manner to guide the catheter to its desired implant location.

System 130 may be at least partially disassembled for loading of a stent assembly onto the balloons 132, 134. For example, a connector 138, which extends generally from one end of balloons 132, 134 and is attached to the guide wire 136 at its opposite end, can be disconnected from the guide wire to provide two separate balloons 132, 134 onto which two barrels of a double-barreled stent can be positioned. The stent barrels may then be crimped or compressed around the balloons 132, 134 until they are the desired size for implanting into a patient, and the connector 138 can then be reattached to the guide wire 136 and the system 130 can be inserted into the patient. When the components of the system 130 are positioned relative to the mitral valve area of the patient, balloons 132, 134 may be inflated to thereby expand the compressed stent barrels to the desired size relative to the mitral valve annulus. After such stent expansion is complete, the balloons 132, 134 can be deflated and the system 130 can then be withdrawn from the patient.

System 130 may further include one or more elongated sheaths (not shown) positioned over the catheter, which are large enough to surround one or both compressed sheaths when they are located over the balloon 132, 134. In their open or deployed configurations, each sheath is positioned along the catheter length so that balloons 132, 134 are not constrained and are therefore able to be inflated. Sliding each sheath toward the distal end of the system 130 so that it covers one or both balloons would provide a closed position of the device 10, which is the configuration in which the device would typically be inserted into a patient.

As discussed above, at least one embodiment of the present invention includes a stent assembly having a single barrel, such as is shown in FIGS. 15-18, for example. If such a single-barreled stent is to be implanted into a body opening that is not circular in shape, one exemplary delivery and stent-expansion device 200 that can be used for implantation of the stent is illustrated in FIGS. 22 and 23. Device 200 generally includes a multi-balloon structure consisting of a central balloon 202, two side balloons 204, 206, and an outer balloon 208. Because the side balloons 204, 206 are located on opposite sides of central balloon 202, the width of the device 200 along a first axis 210 is larger than the height of the device 200 along a second axis 212 that is generally perpendicular to the first axis 210. This type of arrangement is particularly adaptable to a stent that has a generally elliptical or oval shape, such as may be used in the replacement of a mitral valve, although it can be used for other stent opening shapes.

The relative sizes of the multiple balloons may vary from the arrangement shown, depending on the shape and size of the stent in which the device 200 will be positioned. For example, in order to achieve an elliptical shape, the side balloons 204, 206 will preferably be at least slightly smaller than the central balloon 202. However, if the shape of the stent is not elliptical, the side balloons 204, 206 may be roughly the same size as the central balloon 202 and/or each of the side balloons 204, 206 may be identically or differently sized and shaped as the other of the side balloons 204, 206. The three balloons 202, 204, 206 can be independently expandable or may be connected to each other for simultaneous expansion of all the balloons. To provide more customizable balloon inflation, the balloons 202, 204, 206 will have their own inflation controls, which can be particularly useful to allow a surgeon to adjust the expansion of the stent in which it is being used. Whether or not the balloons 202, 204, 206 are independently inflatable, these inner balloons are preferably expanded prior to inflation of the outer balloon 208. That is, the balloons 202, 204, 206 are first inflated to expand a stent to its desired shape and size, then the outer balloon 208 is inflated to essentially "lock" or seal the stent in place. Due to the configuration of the inner balloons 202, 204, 206, the outer balloon 208 will generally conform to the outermost bounds of the inner balloons, thus maintaining a shape that is not circular. However, the outer balloon 208 provides additional pressure against the inside of the stent, such as stent 214 in FIG. 22, to keep the stent in its desired location. Once the stent is expanded, the balloons 202, 204, 206, 208 can be deflated and removed from the stent.

While the description of the device 200 includes three inner balloons and one outer balloon, it is contemplated that the delivery devices of the invention may include more or less than three inner balloons and/or that the inner balloons may be positioned differently than shown and described. Further, the outer balloon (e.g., balloon 208) may not be included as part of the delivery device, if desired. In another alternative, more than one outer balloon may be used to encompass some or all of the inner balloons. As with other delivery systems of the invention, the delivery device 200 may use fluids for inflation of the balloons, such as a radio-opaque fluid, during the process of deploying a stent assembly within a patient.

FIGS. 24 and 25 illustrate another embodiment of a stent 220 having a single barrel construction. Stent 220 is shown as having a generally circular shape; however, other shapes for the stent are also contemplated, such as elliptical, oval, or another shape that corresponds with an implantation site in a patient. Stent 220 includes a series of wires arranged as multiple zigzag structures having adjacent generally straight sections that meet one another at a curved or angled junction to form a "V" or "U" shaped structure, although other wire arrangements are contemplated. In any case, stent 220 includes a reinforced area 222, which may be provided through the use of a wire that is thicker than the remaining wires in the structure, for example. Alternatively, reinforced area 222 may be provided as another structure made of the same or a different material than the other wires of the stent 220, where the reinforced area 222 will be relatively stiff and/or constrained as compared to the areas above and below reinforced area 222. For example, the reinforced area 222 may include a sealing gasket, such as tissue, fabric, polymer, metal mesh, or the like. In this way, the stent 220 can be designed so that the area 222 is the desired size for the annulus in which it will be positioned, while allowing the areas above and below the area 222 to expand or flare to a larger size to help to anchor the stent 220 in place. In addition, the stent 220, or any of the embodiments of stents described herein relative to the invention (including double-barreled stents), may include a gasket or other member around its exterior to provide for sealing against paravalvular leakage and to facilitate pannus in-growth for stabilization of the stent. Such a gasket or other member may alternatively or additionally be positioned on the interior portion of the stent or on the underside of a cuff provided on the stent.

FIG. 25 illustrates an exemplary delivery system for expanding the stent 220 as described above. In particular, the delivery system includes one or more balloons, where a balloon or portion of a balloon 224 is positioned on one side of the stent 220 and a balloon or portion of a balloon 226 is positioned on the opposite side of the stent 220. As shown, the stent 220 is relatively smaller in diameter at its reinforced or central area 222 than at the flared areas near the top and bottom of the stent 220. Thus, the balloon portions 224, 226 are relatively expandable to provide the necessary pressure to push the stent outwardly in this manner.

The stent assemblies of the present invention may be positioned within the desired area of the heart via entry in a number of different ways. In one example, the stent assembly may be inserted transatrially, where entry may be done either percutaneously or in a minimally invasive technique on a beating heart in which access is through the side of the heart, or even through a standard open heart valve replacement procedure using heart-lung bypass and sternotomy where the described device would be used as an alternative to the standard replacement. In another example, the stent assembly may be inserted transapically, where entry again may be done either percutaneously or in a minimally invasive technique on a beating heart in which access is through the side of the heart. In yet another example, the stent assembly may be inserted transeptally, where entry can be done percutaneously, such as via the venous system into the right atrium and across a small hole in the septum to enter the left atrium. It is also possible that the delivery approaches may include balloons that would be used to facilitate the crossing of the mitral valve, thereby avoiding entanglement in the mitral apparatus.

Although the description of the stent barrels herein is primarily directed to stents that are expanded through pressure from an expandable balloon positioned therein, it is also contemplated that the stent barrels of the present invention are self-expanding such that pressure is required to maintain the stent in its compressed condition, and removal of such pressure will allow these stents to expand to their desired size. In these cases, the delivery system will be somewhat different than that described above relative to stents that are not self-expanding, and will instead include a system that only requires removal of external pressure (e.g., a compressive sheath) to allow the stents to expand, such as is the case with the delivery of stent grafts for aneurysms in the ascending aorta. These systems may also incorporate means for recapturing and/or repositioning the stent, if desired. In any case, it may be desirable to measure the mitral valve area with some type of spacer prior to installing the actual stent assembly in the heart of the patient.

The stent assemblies of the invention may further include a means of facilitating orientation of the assembly, which can be particularly advantageous in cases where the stent assemblies include asymmetric features and configurations that must be properly oriented relative to the anatomy of the patient. To that end, the stent assemblies may include portions with materials that are opaque when viewed with various imaging techniques, such as echogenic coatings and radiopaque metals and polymers. Additionally or alternatively, the material used to fabricate the stent itself may be highly visible when using certain imaging techniques so that the user has a clear visibility of the orientation of the device prior to and during deployment.

The present invention has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein.

What is claimed is:

1. A method comprising:
positioning a valve prosthesis in an area of a heart valve of a patient, the valve prosthesis including a stent assembly and a prosthetic valve disposed within the stent assembly, the stent assembly including a downstream edge defined by downstream apices of the stent assembly, the downstream edge defining a downstream plane around an entire perimeter of the stent assembly, wherein the downstream plane is at a non-perpendicular angle to a central longitudinal axis of the stent assembly, the valve prosthesis positioned such that the downstream plane is angled in a downstream direction from a first portion of the heart valve towards a second portion of the heart valve; and
radially expanding the valve prosthesis in the area of the heart valve.

2. The method of claim 1, wherein the heart valve is a mitral valve, and wherein the first portion of the heart valve is an anterolateral portion of the mitral valve and the second portion of the heart valve is a posteromedial portion of the mitral valve.

3. The method of claim 2, wherein the first length is such that the stent assembly minimizes interference with the function of an aortic valve adjacent the mitral valve and provides sufficient contact area to impede dislodging of the stent assembly.

4. The method of claim 1, wherein the heart valve is a tricuspid valve, and wherein the first portion of heart valve is an anterior annulus of the tricuspid valve.

5. The method of claim 1, wherein the heart valve is a tricuspid valve, and wherein the first portion of heart valve is a septal annulus of the tricuspid valve.

6. The method of claim 1, wherein the heart valve is a tricuspid valve, and wherein the first portion of heart valve is an anteroseptal commissure of the tricuspid valve.

7. The method of claim 1,
wherein the stent assembly comprises a single stent having a first open end and a second open end, wherein the downstream edge is at the second open end.

8. The method of claim 1,
wherein the stent assembly is balloon expandable,
wherein the positioning step comprises percutaneously delivering the valve prosthesis mounted on a balloon of a balloon catheter, and
wherein the step of radially expanding the valve prosthesis comprises inflating the balloon of the balloon catheter.

9. The method of claim 1,
wherein the stent assembly is self-expanding,
wherein the positioning step comprises percutaneously delivering the valve prosthesis in a radially compressed configuration disposed within a compressive sheath, and
wherein the radially expanding step comprises removing the compressive sheath from around the valve prosthesis, thereby allowing the stent assembly to self-expand.

10. A method comprising:
positioning a valve prosthesis in an area of a heart valve of a patient, the valve prosthesis including a stent assembly and a prosthetic valve disposed within the stent assembly, the stent assembly including a first open end at a first longitudinal end of the stent assembly and a second open end at a second longitudinal end of the stent assembly, wherein a first edge of the stent assembly defines the first open end and a second edge of the stent assembly defines the second open end, wherein the second edge defines a plane around an entire perimeter of the stent assembly, wherein the plane is at a non-perpendicular angle to a central longitudinal axis of the stent assembly, the valve prosthesis positioned such that the plane is angled in a downstream direction from a first portion of the heart valve towards a second portion of the heart valve; and
radially expanding the valve prosthesis in the area of the heart valve.

11. The method of claim 10, wherein the first open end is an upstream end, first edge is an upstream edge, the second open end is a downstream end, the second edge is a downstream edge, and the plane is a downstream plane.

12. The method of claim 10, wherein the heart valve is a mitral valve, and wherein the first portion of the heart valve is an anterolateral portion of the mitral valve and the second portion of the heart valve is a posteromedial portion of the mitral valve.

13. The method of claim 12, wherein the first length is such that the stent assembly minimizes interference with the function of an aortic valve adjacent the mitral valve and provides sufficient contact area to impede dislodging of the stent assembly.

14. The method of claim 10, wherein the heart valve is a tricuspid valve, and wherein the first portion of heart valve is an anterior annulus of the tricuspid valve.

15. The method of claim 10, wherein the heart valve is a tricuspid valve, and wherein the first portion of heart valve is a septal annulus of the tricuspid valve.

16. The method of claim 10, wherein the heart valve is a tricuspid valve, and wherein the first portion of heart valve is an anteroseptal commissure of the tricuspid valve.

17. The method of claim 10, wherein the stent assembly comprises a single stent.

18. The method of claim 10,
wherein the stent assembly is balloon expandable,
wherein the positioning step comprises percutaneously delivering the valve prosthesis mounted on a balloon of a balloon catheter, and
wherein the step of radially expanding the valve prosthesis comprises inflating the balloon of the balloon catheter.

19. The method of claim 10,
wherein the stent assembly is self-expanding,
wherein the positioning step comprises percutaneously delivering the valve prosthesis in a radially compressed configuration disposed within a compressive sheath, and
wherein the radially expanding step comprises removing the compressive sheath from around the valve prosthesis, thereby allowing the stent assembly to self-expand.

* * * * *